United States Patent
Xing et al.

(10) Patent No.: US 9,513,235 B2
(45) Date of Patent: Dec. 6, 2016

(54) X-RAY DUAL-ENERGY CT RECONSTRUCTION METHOD

(71) Applicants: TSINGHUA UNIVERSITY, Beijing (CN); NUCTECH COMPANY LIMITED, Beijing (CN)

(72) Inventors: Yuxiang Xing, Beijing (CN); Le Shen, Beijing (CN); Li Zhang, Beijing (CN); Zhiqiang Chen, Beijing (CN); Liang Li, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 212 days.

(21) Appl. No.: 14/337,209

(22) Filed: Jul. 22, 2014

(65) Prior Publication Data

US 2015/0030225 A1    Jan. 29, 2015

(30) Foreign Application Priority Data

Jul. 26, 2013    (CN) .......................... 2013 1 0318608

(51) Int. Cl.
*G01N 23/04* (2006.01)
*G06T 11/00* (2006.01)

(52) U.S. Cl.
CPC ........... *G01N 23/046* (2013.01); *G06T 11/006* (2013.01); *G06T 2207/10081* (2013.01);
(Continued)

(58) Field of Classification Search
CPC .................. G06T 11/003; G06T 11/006; G06T 2207/10081; G06T 2211/408; G01N 23/046; A61B 6/482; A61B 6/5205
See application file for complete search history.

(56) References Cited

U.S. PATENT DOCUMENTS 9,036,879 B2 *   5/2015  Mendonça et al. ..  A61B 6/4241
                                                              378/4
2010/0284514 A1 *  11/2010  Zhang et al. ................... 378/53
(Continued)

OTHER PUBLICATIONS

Xing et al.; "A reconstruction method for dual high-energy CT with MeV X-Rays"; IEEE Trans Nucl. Sci.; vol. 58 No. 8; Apr. 2011; p. 537-546.
(Continued)

*Primary Examiner* — Andrew W Johns
(74) *Attorney, Agent, or Firm* — Baker & Hostetler LLP

(57) ABSTRACT

The present disclosure relates to a self-prior information based X-ray dual-energy CT reconstruction method, which can utilize information inherent in data to provide a prior model, thereby obtaining a reconstructed image with a high quality. The X-ray dual-energy CT reconstruction method according to the present disclosure comprises: (a) rating an energy spectrum and establishing a dual-energy lookup table; (b) collecting high-energy data $p_H$ and low-energy data $p_L$ of a dual-energy CT imaging system using a detector of the dual-energy CT imaging system; (c) obtaining projection images $R_1$ and $R_2$ of scaled images $r_1$ and $r_2$ according to the obtained high-energy data $p_H$ and low-energy data $p_L$; (d) reconstructing the scaled image $r_2$ using a first piece-wise smooth constraint condition and thereby obtaining an electron density image; and (e) reconstructing the scaled image $r_1$ using a second piece-wise smooth constraint condition and thereby obtaining an equivalent atomic number image. In the present disclosure, the noise in the dual-energy reconstructed image can be effectively prohibited while keeping the resolution by effectively using information inherent in data.

11 Claims, 2 Drawing Sheets

(52) U.S. Cl.
CPC ............... *G06T 2207/20182* (2013.01); *G06T 2207/30004* (2013.01); *G06T 2211/408* (2013.01); *G06T 2211/424* (2013.01)

(56) References Cited

U.S. PATENT DOCUMENTS

2011/0188725 A1* 8/2011 Yu et al. ........................ 382/131
2015/0356755 A1* 12/2015 Shen et al. ............ G06T 11/005
378/19

OTHER PUBLICATIONS

Zhang; "Research on the Method and Application of Dual Energy X-Ray Imaging"; Engineering Physics at Tsinghua University; 2008; contains abstract; 129 pages.

Zhang et al.; "Exact Reconstruction for Dual Energy Computed Tomography Using an H-L Curve Method:"; IEEE Nuclear Science Symposium Conf. Record; vol. 6; 2006; p. 3485-3488.

* cited by examiner (a)   (b)

X-RAY DUAL-ENERGY CT RECONSTRUCTION METHOD

CROSS-REFERENCE TO RELATED APPLICATIONS

This application claims priority to Chinese Patent Application No. 201310318608.4 filed Jul. 26, 2013, the disclosure of which are incorporated herein by reference in its entirety.

TECHNICAL FIELD

The present disclosure relates to a Computer Tomography (CT) reconstruction method, and in particular, to self-prior information based X-ray dual-energy CT reconstruction methods.

BACKGROUND

A CT image contrast is largely related to an X-ray source energy spectrum distribution used for scanning. The traditional CT uses a ray source with an energy spectrum distribution for imaging. Sometimes, information ambiguity may occur, which results in two different materials being completely the same on a CT image. The dual-energy CT uses two energy spectrums with different distributions for imaging an object, which can eliminate the information ambiguity in a single energy spectrum. The dual-energy X-ray CT imaging technology can utilize difference between attenuations of a material at different energy levels to obtain distribution information about multiple physical characteristic parameters of an object, for example, an electron density distribution, an equivalent atomic number distribution, and single-energy attenuation images at multiple energy levels. Thus, the dual-energy X-ray CT can be used for calibration of ray hardening of the traditional CT, acquisition of a clinical energy spectrum image with a high contrast, detection of particular and dangerous goods in industry and safety inspection and so on. Compared with the traditional X-ray CT imaging technology, breakthroughs of the dual-energy CT in its imaging function are of great significance in applications such as a medical diagnosis technology, lossless detection and safety inspection etc., and thus attract more and more attention in recent years. In addition, the dual-energy X-ray CT reconstruction method is a search hotspot currently.

Currently, there are three methods for dual-energy CT reconstruction as follows: (1) a post-processing method, in which attenuation coefficient distribution images are reconstructed from low-energy data and high-energy data respectively, then synthesis calculation is performed on the two attenuation coefficient distribution images, and thereby, a single-energy image or a distribution image of an energy independent physical quantity (for example, an atomic number, an electron density) can be obtained; (2) a pre-processing method, in which an energy dependent signal and an energy independent signal are parsed from low-energy data and high-energy data (i.e., the so-called dual-energy decomposition), wherein, the parsed signals belong to a projection region, and then, the parsed signals are reconstructed using a traditional CT reconstruction method; and (3) a synthesis iterative method, in which low-energy data and high-energy data are reconstructed directly using an iterative method. At present, the pre-processing method is widely used, because on one hand, the pre-processing method is more accurate than the post-processing method, and can better eliminate an effect of an x-ray broad spectrum; and on the other hand, the pre-processing method has a less calculation amount than the synthesis iterative method.

At present, with respect to the dual-energy decomposition, there are two decomposition methods, i.e., material based decomposition and dual-effect decomposition (for example, with reference to a non-patent document 1). However, in the dual-effect decomposition method, the equivalent atomic number reconstructed image generally has a poor signal-to-noise ratio, and in contrast, the electron density image has a better signal-to-noise ratio (for example, with reference to a non-patent document 2). In addition, in the dual-energy CT reconstruction, a MonteCarlo method or an experiential method can be used for estimating energy spectrum data of the dual-energy CT system, and moreover, a lookup table can also be established (for example, with reference to non-patent documents 2 and 3).

Prior Art Documents

Non-patent document 1: Y. Xing, L. Zhang, X. Duan, J. Cheng, Z. Chen, "A reconstruction method for dual high-energy CT with Mev X-rays," IEEE Trans Nucl. Sci. vol. 58, no. 2, pp 537-546, 2011;

Non-patent document 2: Guowei Zhang, dual-energy X-ray imaging algorithm and application research [D], Beijing: Engineering Physics at Tsinghua University, 2008; and Non-patent document 3: G. Zhang, Z. Chen, L. Zhang, and J. Cheng, Exact Reconstruction for Dual Energy Computed Tomography Using an H-L Curve Method, 2006 IEEE Nuclear Science Symposium Conference Record, pp. M14-462, 2006.

In addition, in the dual-energy CT reconstruction, two primary physical characteristic parameters are an equivalent atomic number and an electronic density. Since there is strong unbalance in a process of the dual-energy decomposition, it results in amplification of a noise of the dual-energy CT reconstructed image, especially amplification of a noise of the equivalent atomic number distribution.

SUMMARY

The present disclosure is proposed to solve the above problem. The purpose of the present disclosure is to provide dual-energy CT reconstruction methods, which can provide a prior model using information inherent in data, so as to obtain a reconstructed image with a high quality.

The present disclosure provides an X-ray dual-energy CT reconstruction method, comprising:

(a) collecting high-energy data $p_H$ and low-energy data $p_L$ of a dual-energy CT imaging system using a detector of the dual-energy CT imaging system;

(b) obtaining projection images $R_1$ and $R_2$ of scaled images $r_1$ and $r_2$ according to the obtained high-energy data $p_H$ and low-energy data $p_L$;

(c) reconstructing the scaled image $r_2$ using a first piece-wise smooth constraint condition and obtaining a decomposition coefficient $a_2$; and (d) reconstructing the scaled image $r_1$ using a second piece-wise smooth constraint condition and obtaining a decomposition coefficient $a_1$.

In addition, in the X-ray dual-energy CT reconstruction method according to the present disclosure, the scaled images $r_1$ and $r_2$ are defined in equation (4) as follows:

$$r_1 \equiv \mathrm{diag}\left(\frac{1}{\omega_1 + \varepsilon}\right) a_1 \qquad (4)$$

-continued $$r_2 \equiv \text{diag}\left(\frac{1}{\omega_2 + \varepsilon}\right) a_2$$

the projection images $R_1$ and $R_2$ are defined in equation (6) as follows:

$$R_1 \equiv H'_1 r_1$$

$$R_2 \equiv H'_2 r_2 \qquad (6)$$

wherein, $H'_1 \equiv H \text{diag}(\omega_1 + \varepsilon)$ and $H'_2 \equiv H \text{diag}(\omega_2 + \varepsilon)$, in which H is a projection matrix, $a_1$ and $a_2$ are decomposition coefficients, $\varepsilon$ is a vector with small constant coefficients, and $\omega_1$ and $\omega_2$ are vectors which can be selected randomly, in the step (c), $r_2$ is reconstructed using the following equation (9) as the first piece-wise smooth constraint condition:

$$\min_{r_2} \|\nabla r_2\|_p \quad \text{s.t.} \quad R_2 \equiv H'_2 r_2 \qquad (9)$$

and in the step (d), $r_1$ is reconstructed using the following equation (8) as the second piece-wise smooth constraint condition:

$$\min_{r_1} \|\nabla r_1\|_p \quad \text{s.t.} \quad R_1 \equiv H'_1 r_1. \qquad (8)$$

In addition, in the X-ray dual-energy CT reconstruction method according to the present disclosure, in the step (c), an effective linear attenuation coefficient $\mu_H$ at a high energy level is reconstructed according to the high-energy data $p_H$, $\omega_2 = \mu_H$ is selected, and $r_2$ is reconstructed using equation (9) as the first piece-wise smooth constraint condition.

In addition, in the X-ray dual-energy CT reconstruction method according to the present disclosure, in the above step (d), $\omega_1 = a_2$ is set and $r_1$ is reconstructed using equation (8) as the second piece-wise smooth constraint condition.

In addition, in the X-ray dual-energy CT reconstruction method according to the present disclosure, the method further comprises:

obtaining an electronic density image $\rho_e$ according to $a_2 = r_2 \times \text{diag}(\omega_2 + \varepsilon)$ and $\rho_e = 2a_2$ using dual-effect decomposition.

In addition, in the X-ray dual-energy CT reconstruction method according to the present disclosure, the method further comprises:

obtaining an equivalent atomic number image $Z^{eff}$ according to $$Z^{eff} \approx r_1^{\frac{1}{\lambda-1}}, \lambda \approx 4$$

using dual-effect decomposition.

In addition, in the X-ray dual-energy CT reconstruction method according to the present disclosure, the method further comprises:

obtaining an equivalent atomic number image $Z^{eff}$ according to $$Z^{eff} \approx r_1^{\frac{1}{\lambda-1}}, \lambda \approx 4$$

using dual-effect decomposition.

In addition, in the X-ray dual-energy CT reconstruction method according to the present disclosure, in the step (d), an effective linear attenuation coefficient $\mu_H$ at a high energy level is reconstructed according to the high-energy data $p_H$, $\omega_1 = \mu_H$ is set, and $r_1$ is reconstructed using the following equation (8) as the second piece-wise smooth constraint condition:

$$\min_{r_1} \|\nabla r_1\|_p \quad \text{s.t.} \quad R_1 \equiv H'_1 r_1, \qquad (8)$$

then an equivalent atomic number image $Z^{eff}$ is obtained using $a_1 = r_1 \times \text{diag}(\omega_1 + \varepsilon)$ and $$Z^{eff} \approx r_1^{\frac{1}{\lambda-1}}, \lambda \approx 4.$$

In addition, in the X-ray dual-energy CT reconstruction method according to the present disclosure, in the steps (c) and (d), $r_1$ and $r_2$ are reconstructed using an ART+TV method.

In addition, in the X-ray dual-energy CT reconstruction method according to the present disclosure, in the steps (c) and (d), $r_1$ and $r_2$ are reconstructed using a split Bregman method.

Compared with the prior art, the present disclosure has the following effects: (1) the noise in the dual-energy reconstructed image can be effectively prohibited while keeping the resolution by effectively using information inherent in data (for example, $\omega_1$ and $\omega_2$ are selected as $\mu_H$ or $\mu_L$, or $\omega_1$ is selected as $a_2$); (2) the algorithm can conveniently be designed by establishing reconstruction by means of a prior model; and (3) the method is not limited to one scanning method, and is also suitable for different scanning methods such as a fan beam, a cone beam, a circular orbit, a spiral orbit etc., and can increase robustness of iterative reconstruction using this prior method; and (4) compared with a dual-effect decomposition method in the art, a more stable result can be obtained by directly reconstructing a ratio of the coefficients.

DETAILED DESCRIPTION OF THE PREFERRED EMBODIMENTS

Figure 1:
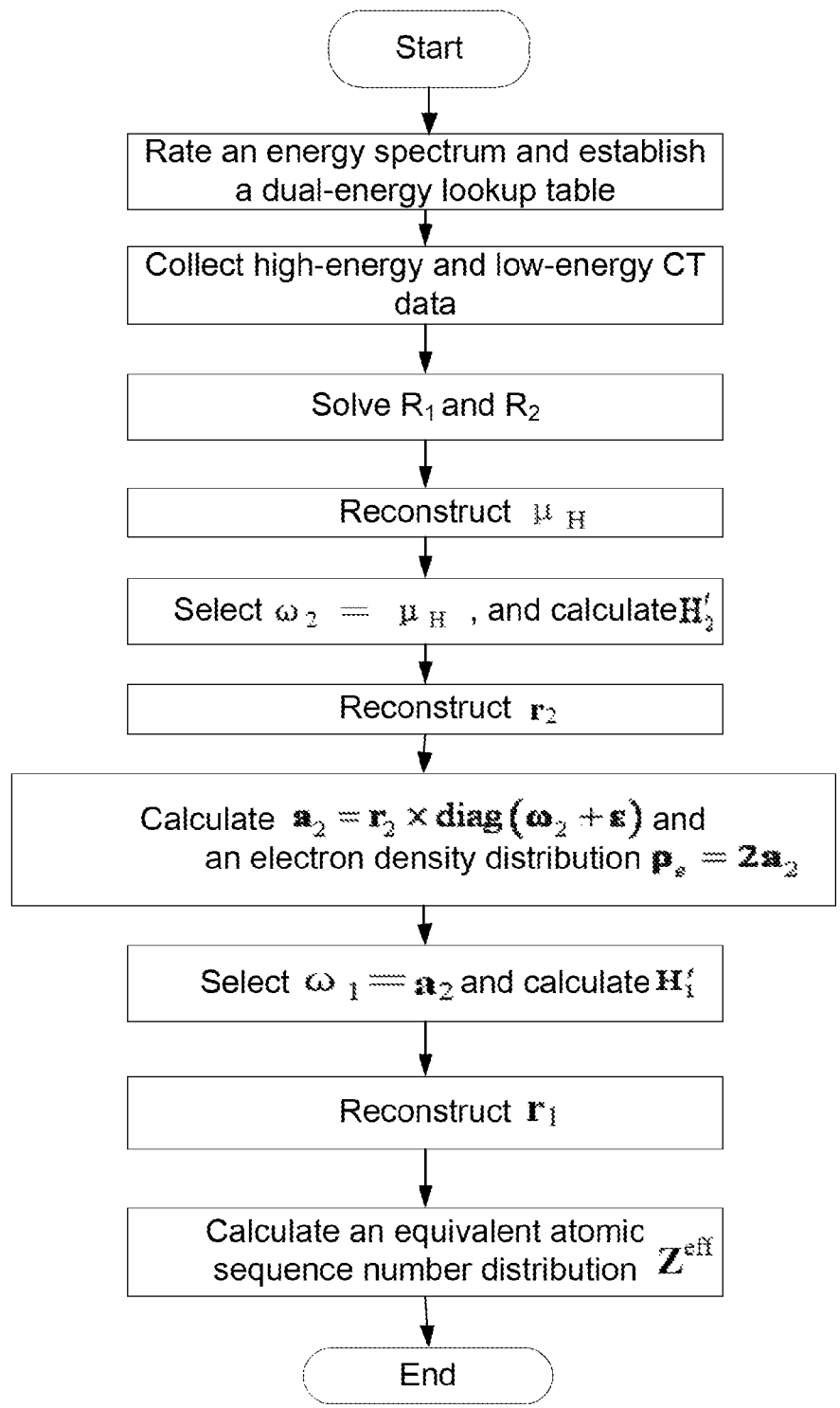
FIG. 1 is a flowchart of a self-prior information based dual-energy CT reconstruction method with dual-effect decomposition as an example according to the present disclosure.

With respect to "self-prior", it is a term proposed by the inventor, since a prior model used in the process of reconstructing the following scaled images $r_1$ and $r_2$ can be obtained from the data per se, for example, a linear attenuation coefficient result obtained by reconstructing single high-energy data previously using a traditional CT method or $\omega_1 = a_2$ ($a_2$ is also a decomposition coefficient) used when reconstructing $a_1$ (a decomposition coefficient), i.e., structural information of $a_2$ is used as prior information. In addition, in the present disclosure, the data per se is processed to obtain reconstruction of a single-energy attenuation image or reconstruction of $a_2$, which are placed in a prior model. Therefore, this is referred to as utilization of information inherent in the data, and thereby, a reconstructed image with a high quality can be obtained.

The embodiments of the present disclosure will be described below with reference to accompanying drawings.

First of all, an energy spectrum is rated and a dual-energy lookup table is established. Then, a detector of a dual-energy CT imaging system is used to collect high-energy data and low-energy data of the dual-energy CT imaging system. Here, assume that the high-energy data and the low-energy data of the dual-energy CT are $p_H$ and $p_L$ respectively, wherein, $p_H$ and $p_L$ are represented by equations (1) and (2) as follows:

$$-\ln \int w_H(E)\exp(-H\mu(E))dE = p_H \quad (1)$$

$$-\ln \int w_L(E)\exp(-H\mu(E))dE = p_L \quad (2)$$

wherein, $w_H(E)$ and $w_L(E)$ in the above equations (1) and (2) are normalized high-energy and low-energy energy spectrum distributions, which can be generated in many ways, including two energy spectrums generated by a pseudo-dual-energy and fast-switch X-ray machine of a dual-layer sandwich detector or energy spectrum distributions obtained using two X-ray machines. In addition, $\mu(E)$ is a linear attenuation coefficient of an object, and H is a projection matrix. According to the traditional CT reconstruction method, estimated values $\hat{\mu}_H$ and $\hat{\mu}_L$ of effective linear attenuation coefficient distributions $\mu_H$ and $\mu_L$ at a high energy level and a low energy level can be obtained, $\hat{\mu}_H$ and $\hat{\mu}_L$ can be used as prior information.

At present, in the art, the dual-energy decomposition includes two decomposition methods, i.e., material based decomposition and dual-effect decomposition. In addition, both decompositions can be expressed as equation (3) as follows:

$$\mu(E) = a_1\phi_1(E) + a_2\phi_2(E) \quad (3)$$

wherein, $\phi_1(E)$ and $\phi_2(E)$ in the above equation (3) are in different predetermined function forms in the material based decomposition and the dual-effect decomposition, and in addition, $a_1$ and $a_2$ are decomposition coefficients.

In addition, two new vectors are introduced in the method according to the present disclosure, i.e., scaled images $r_1$ and $r_2$, which are expressed by equation (4) as follows:

$$r_1 \equiv \text{diag}\left(\frac{1}{\omega_1 + \varepsilon}\right) a_1$$

$$r_2 \equiv \text{diag}\left(\frac{1}{\omega_2 + \varepsilon}\right) a_2 \quad (4)$$

In the above equation (4), diag( ) represents a diagonal matrix, and elements on a diagonal thereof are values of the vector in the parentheses, $\varepsilon$ is a vector with small constant coefficients, to avoid occurrence of a zero value in the denominator, and $\omega_1$ and $\omega_2$ are two vectors which can be selected randomly. In addition, $H'_1 \equiv H\text{diag}(w_1 + \varepsilon)$ and $H'_2 \equiv H\text{diag}(\omega_2 + \varepsilon)$ are defined, and in combination with the above equations (1)-(4), equation (5) can be obtained as follows:

$$-\ln \int w_H(E)\exp(-H'_1 r_1 \phi_1(E) - H'_2 r_2 \phi_2(E))dE = p_H$$

$$-\ln \int w_L(E)\exp(-H'_1 r_1 \phi_1(E) - H'_2 r_2 \phi_2(E))dE = p_L \quad (5)$$

In addition, assume that $$R_1 = H'_1 r_1$$

$$R_2 = H'_2 r_2 \quad (6)$$

wherein, $R_1$ and $R_2$ are projection images of the scaled images $r_1$ and $r_2$ respectively, and $H'_1$ and $H'_2$ are corresponding projection operators respectively.

Next, equation (5) is simplified using equation (6), to obtain equation (7) as follows:

$$-\ln \int w_H(E)\exp(-R_1\phi_1(E) - R_2\phi_2(E))dE = p_H$$

$$-\ln \int w_L(E)\exp(-R_1\phi_1(E) - R_2\phi_2(E))dE = p_L \quad (7)$$

Here, the above equation (7) can be referred to as data under prior definition of a divisor. In addition, for each pair of collected high-energy data and low-energy data, equation (7) forms a non-linear binary equation set. $(R_1, R_2)$ can be obtained according to $(p_H, p_L)$ by solving this equation set, or $(R_1, R_2)$ can be obtained according to a known data pair $(p_H, p_L)$ by establishing a lookup table using a method similar to that described in the non-patent document 2. The remaining problem is to reconstruct $(r_1, r_2)$ according to $(R_1, R_2)$. It can be known from the above equation (6) that the reconstruction of $(r_1, r_2)$ can be completed using any traditional CT reconstruction method. However, in a case that $(r_1, r_2)$ is reconstructed using a traditional dual-energy CT reconstruction method, since there is strong unbalance in a process of dual-energy decomposition, it results in amplification of a noise of the dual-energy CT reconstructed image, especially amplification of a noise of the equivalent atomic number distribution.

In contrast, the method according to the present disclosure is characterized in that $a_1$ and $\omega_1$ are enabled to have similarity and $a_2$ and $\omega_2$ are enabled to have similarity by constraining piece-wise smooth of $r_1$ and $r_2$, i.e., mathematical expressions thereof can be sparse, which enables improvement of quality of the reconstructed image during reconstruction using such characteristics. Both $a_1$ and $\omega_1$ are images, and similarity therebetween refers to similarity of structures between the images. For example, $\omega_1$ is smooth in a place where $a_1$ is smooth, and $\omega_1$ has an edge in a place where $a_1$ has an edge. In addition, due to similarity of structures between $\omega_1$ and $\omega_2$ and $\mu_H$ or $\mu_L$, $\omega_1$ and $\omega_2$ can be selected as $\mu_H$ or $\mu_L$ (wherein, $\mu_H$ or $\mu_L$ can be reconstructed from $p_H$ and $p_L$ respectively according to a traditional single-energy CT) or other prior images similar to $\omega_1$ and $\omega_2$ (for example, in the present disclosure, $a_2$ can be used in the dual-effect decomposition method). In addition, in a case that both $\omega_1$ and $\omega_2$ are uniform constant vectors, this method is degraded to a normal dual-energy reconstruction method. In addition, in the present disclosure, in order to improve the quality of the reconstructed image, piece-wise smooth constraints on $r_1$ and $r_2$ are implemented by using the following conditions, i.e., equation (8) (a second piece-wise smooth constraint condition) and equation (9) (a first piece-wise smooth constraint condition), $$\min_{r_1}\|\nabla r_1\|_p \text{ s.t. } R_1 \equiv H'_1 r_1 \qquad (8)$$

$$\min_{r_2}\|\nabla r_2\|_p \text{ s.t. } R_2 \equiv H'_2 r_2 \qquad (9)$$

In the above equations (8) and (9), $\|\nabla r\|_p$ represents a p-order norm of a gradient of r. Here, piece-wise smooth of r is implemented by minimization of $\|\nabla r\|_p$.

In addition, in the above equations (8) and (9), except for subscripts, the expressions are totally the same. Therefore, reconstructions of $r_1$ and $r_2$ can be implemented independently using the same method. However, on the other hand, in terms of the dual-energy CT, in order to optimize the quality of the reconstructed image, the selection of $\omega_1$ and $\omega_2$ can be optimized respectively from the characteristics of the dual-energy CT according to practical conditions. For example, for a dual-effect decomposition method (with reference to the non-patent document 2), the equivalent atomic number reconstructed image generally has a poor signal-to-noise ratio, and in contrast, the electron density image has a better signal-to-noise ratio. In addition, based on the dual-effect decomposition method, calculation equations of an equivalent atomic number $Z^{eff}$ and an electron density $\rho_e$ are as shown in equation (10) as follows:

$$Z^{eff} = \left(\text{diag}\left(\frac{1}{a_2}\right)a_1\right)^{\frac{1}{\lambda-1}}, \lambda \approx 4 \qquad (10)$$

$$\rho_e = 2a_2$$

wherein, $\lambda$ is a parameter indicating a change of an photo-electric effect with energy in the dual-effect decomposition, and $\omega_1 = a_2$ can be selected. Thus, the following equation (11) is obtained:

$$Z^{eff} \approx r_1^{\frac{1}{\lambda-1}}, \lambda \approx 4 \qquad (11)$$

Thus, a noise level of the equivalent atomic number reconstructed image can be better controlled, since a value of the equivalent atomic number can be enabled to be relatively stable by constraining piece-wise smooth of $r_1$.

Here, in the present disclosure, specifically by taking the dual-energy CT reconstruction based on dual-effect decomposition as an example, the following specific embodiments are given using the method according to the present disclosure.

Figure 2:
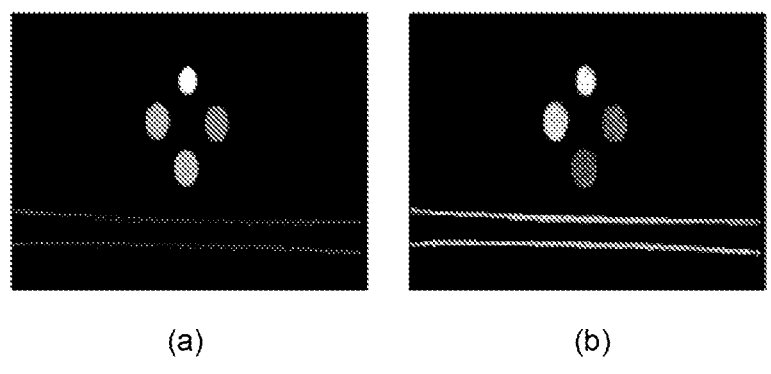
FIG. 2 is an image obtained by reconstruction using a self-prior information based dual-energy CT reconstruction method with dual-effect decomposition as an example according to the present disclosure, wherein, (a) is an electron density reconstructed image, and (b) is an equivalent atomic number reconstructed image.

FIG. 1 is a flowchart of a self-prior information based dual-energy CT reconstruction method with dual-effect decomposition as an example. FIG. 2 is an image obtained by reconstruction using a self-prior information based dual-energy CT reconstruction method with dual-effect decomposition as an example, wherein, (a) is an electron density reconstructed image, and (b) is an equivalent atomic number reconstructed image.

In the present embodiment, as shown in FIG. 1, first of all, an energy spectrum is rated and a dual-energy lookup table is established. With respect to establishment of a lookup table, determined known materials are made to have different thicknesses, and thereby, ($R_1$, $R_2$) are known. Then, these materials are placed into the dual-energy CT system for data collection, so as to obtain ($p_H$, $p_L$). A table is generated using these data. In general, more than two materials and dozens of thicknesses are used. Published documents in the art (for example, the non-patent document 2) can be referred to for more detailed description.

Then, a detector of a dual-energy CT imaging system is used to collect high-energy data $p_H$ and low-energy data $p_L$ of the dual-energy CT imaging system.

Next, values of projection images $R_1$ and $R_2$ of scaled images $r_1$ and $r_2$ are obtained through a lookup table or according to the above binary equation set (7).

Next, $\mu_H$ is reconstructed from $p_H$ using a traditional single-energy CT reconstruction method, and $\omega_2 = \mu_H$ is selected. That is, structure information of $\mu_H$ is used as prior information.

Next, $H'_2$ is obtained according to the above equation $H'_2 \equiv H\text{diag}(\omega_2+\epsilon)$. Then, $r_2$ is reconstructed according to the above equation (9) (the first piece-wise smooth constraint condition), i.e., $$\min_{r_2}\|\nabla r_2\|_p \text{ s.t. } R_2 \equiv H'_2 r_2.$$

In addition, there are a variety of methods in the art to be selected for implementing the above optimization problem, and the optimization is generally completed by means of iteration. In the present application, the optimization will be described by taking an ART+TV method as an example.

1) Initialize $r_2 = 1$.
n=1, and $r_2^{n,1} = r_2$;
2) For n=2, ..., $N_{iter}$:
ART iterations: for m=2, ..., $N_{ART}$:

$$r_2^{n,m} = r_2^{n,m-1} + H_i \cdot \frac{[R'_2]_i - [H]_i \cdot r_2^{n,m-1}}{\|[H]_i\|_2};$$

wherein, i is a ray index number, $[H]_i$ is a vector in an $i^{th}$ row of the system matrix, $N_{iter}$ is a total number of iterations.

3) Apply regularization constraints to each element of the vector $r_2^{n, N_{ART}}$: $r_2^{n, N_{ART}} = \max(r_2^{n, N_{ART}}, 0)$, wherein, $N_{ART}$ is a number of ART iterations.

4) Apply total variation minimization iteration to the vector $r_2^{n, N_{ART}}$:

$$d^n = \|r_2^{n,1} - r_2^{n,N_{ART}}\|_2, \quad r_2^{n,1} = r_2^{n,N_{ART}}$$

Total variation steepest descent method: for k=2, ..., $N_{TV}$, $\alpha = 0.2$, $\epsilon = 10^{-8}$:

$$v^{n,k-1} = \frac{\partial \|r\|_{TV}}{\partial r}\bigg|_{r=r^{n,k-1}},$$

$$v^{n,k-1} = \frac{v^{n,k-1}}{|v^{n,k-1}|};$$

$$r_2^{n,k} = r_2^{n,k-1} - \alpha \cdot d^n \cdot v^{n,k-1};$$

5) $r_2^{n+1, 1} = r_2^{n, N_{TV}}$; return to 2) to start a next iteration, wherein, $N_{TV}$ is a minimized number of iterations for TV.

In addition, as described above, in the present disclosure, except for the above ART+TV method, $r_2$ can also be reconstructed using other methods such as a split Bregman method.

Next, a decomposition coefficient $a_2$ and an electron density $\rho_e$ are obtained according to the above equations (4)

and (10), i.e., $a_2=r_2 \times \text{diag}(\omega_2+\epsilon)$ and $p_e=2a_2$ are calculated. Thereby, an electron density image can be obtained. FIG. 2(a) is an electron density reconstructed image which is obtained as described above. As shown in FIG. 2(a), the edge of the electron density image is clear.

Next, $\omega_1=a_2$ is set, and thereby $H'_1$ is obtained according to the equation $H'_1 \equiv H\text{diag}(a_2+\epsilon)$. That is, structure information of $a_2$ is used as prior information here.

Next, $r_1$ is reconstructed according to the above equation (8) (the second piece-wise smooth constraint condition), i.e., $$\min_{r_1} \|\nabla r_1\|_p \quad \text{s.t.} \quad R_1 \equiv H'_1 r_1.$$

In addition, steps of a specific implementation for reconstructing $r_1$ are the same as those for reconstructing $r_2$ described above.

Next, an equivalent atomic number $$Z^{\textit{eff}} \approx r_1^{\frac{1}{\lambda-1}}$$

is obtained according to equation (11), and thereby, an equivalent atomic number image can be obtained. FIG. 2(b) is an equivalent atomic number reconstructed image which is obtained as described above. As shown in FIG. 2(b), uniformity of the noise of the equivalent atomic number image in a local region of the same material is largely improved, there is no abnormal point, and slim shaped substances can be reconstructed well.

In addition, reconstruction of $r_1$ may also be different from the above. $\omega_1=\mu_H$ is set (i.e., taking structure information of $\mu_H$ as prior information) and $r_1$ is reconstructed using equation (8) as the second piece-wise smooth constraint condition, and then an equivalent atomic number image $Z^{\textit{eff}}$ is obtained using $a_1=r_1 \times \text{diag}(\omega_1+\epsilon)$ and $$Z^{\textit{eff}} = \left(\text{diag}\left(\frac{1}{a_2}\right)a_1\right)^{\frac{1}{\lambda-1}}, \lambda \approx 4.$$

Thus, an equivalent atomic number image with a high quality can also be obtained similarly.

As described above, the present disclosure is described by taking the dual-energy CT reconstruction based on dual-effect decomposition as an example, but it is not limited thereto. The method according to the present disclosure can also be applied to material based decomposition.

As described above, in the present disclosure, the noise in the dual-energy reconstructed image can be effectively prohibited while keeping the resolution by effectively using information inherent in data, and the algorithm can conveniently be designed by establishing reconstruction by means of a prior model. In addition, the method according to the present disclosure is not limited to one scanning method, and is also suitable for different scanning methods such as a fan beam, a cone beam, a circular orbit, a spiral orbit etc., and can increase robustness of iterative reconstruction using this prior method. Moreover, compared with a dual-effect decomposition method in the art, the X-ray dual-energy CT reconstruction method according to the present disclosure obtains a more stable result by directly reconstructing a ratio of the coefficients.

What is claimed is:

1. An X-ray dual-energy CT reconstruction method, comprising:
    (a) collecting high-energy data $p_H$ and low-energy data $p_L$ of a dual-energy CT imaging system using a detector of the dual-energy CT imaging system;
    (b) obtaining projection images $R_1$ and $R_2$ of scaled images $r_1$ and $r_2$ according to the obtained high-energy data $p_H$ and low-energy data $p_L$;
    (c) reconstructing the scaled image $r_2$ using a first piece-wise smooth constraint condition and obtaining a decomposition coefficient $a_2$; and
    (d) reconstructing the scaled image $r_1$ using a second piece-wise smooth constraint condition and obtaining a decomposition coefficient $a_1$.

2. The X-ray dual-energy CT reconstruction method according to claim 1, wherein, the scaled images $r_1$ and $r_2$ are defined in equation (4) as follows:

$$r_1 \equiv \text{diag}\left(\frac{1}{\omega_1+\varepsilon}\right)a_1 \qquad (4)$$

$$r_2 \equiv \text{diag}\left(\frac{1}{\omega_2+\varepsilon}\right)a_2$$

the projection images $R_1$ and $R_2$ are defined in equation (6) as follows:

$$R_1 = H'_1 r_1$$

$$R_2 = H'_2 r_2 \qquad (6)$$

wherein, $H'_1 \equiv H\text{diag}(\omega_1+\epsilon)$ and $H'_2 \equiv H\text{diag}(\omega_2+\epsilon)$, in which H is a projection matrix, $a_1$ and $a_2$ are decomposition coefficients, $\epsilon$ is a vector with small constant coefficients, and $\omega_1$ and $\omega_2$ are vectors which can be selected randomly, in the step (c), $r_2$ is reconstructed using the following equation (9) as the first piece-wise smooth constraint condition:

$$\min_{r_2} \|\nabla r_2\|_p \quad \text{s.t.} \quad R_2 \equiv H'_2 r_2 \qquad (9)$$

and in the step (d), $r_1$ is reconstructed using the following equation (8) as the second piece-wise smooth constraint condition:

$$\min_{r_1} \|\nabla r_1\|_p \quad \text{s.t.} \quad R_1 \equiv H'_1 r_1. \qquad (8)$$

3. The X-ray dual-energy CT reconstruction method according to claim 2, wherein, in the step (c), an effective linear attenuation coefficient $\mu_H$ at a high energy level is reconstructed according to the high-energy data $p_H$, $\omega_2=\mu_H$ is selected, and $r_2$ is reconstructed using equation (9) as the first piece-wise smooth constraint condition.

4. The X-ray dual-energy CT reconstruction method according to claim 2, wherein, in the above step (d), $\omega_1=a_2$ is set and $r_1$ is reconstructed using equation (8) as the second piece-wise smooth constraint condition.

5. The X-ray dual-energy CT reconstruction method according to claim 4, further comprising:

obtaining an electron density image $\rho_e$ according to $a_2=r_2 \times \text{diag}(\omega_2+\epsilon)$ and $\rho_e=2a_2$ using dual-effect decomposition.

6. The X-ray dual-energy CT reconstruction method according to claim 4, further comprising:
obtaining an equivalent atomic number image $Z^{\text{eff}}$ according to $$Z^{\text{eff}} \approx r_1^{\frac{1}{\lambda-1}}, \lambda \approx 4$$

using dual-effect decomposition.

7. The X-ray dual-energy CT reconstruction method according to claim 2, further comprising:
obtaining an electronic density image $\rho_e$ according to $a_2=r_2 \times \text{diag}(\omega_2+\epsilon)$ and $\rho_e=2a_2$ using dual-effect decomposition.

8. The X-ray dual-energy CT reconstruction method according to claim 2, further comprising:
obtaining an equivalent atomic number image $Z^{\text{eff}}$ according to $$Z^{\text{eff}} \approx r_1^{\frac{1}{\lambda-1}}, \lambda \approx 4$$

using dual-effect decomposition.

9. The X-ray dual-energy CT reconstruction method according to claim 2, wherein, in the step (d), an effective linear attenuation coefficient $\mu_H$ at a high energy level is reconstructed according to the high-energy data $p_H$, $\omega_1=\mu_H$ is set, and $r_1$ is reconstructed using the following equation (8) as the second piece-wise smooth constraint condition:

$$\min_{r_1} \|\nabla r_1\|_p \quad \text{s.t.} \quad R_1 \equiv H_1' r_1, \tag{8}$$

then, an equivalent atomic number image $Z^{\text{eff}}$ is obtained using $a_1=r_1 \times \text{diag}(\omega_1+\epsilon)$ and $$Z^{\text{eff}} \approx r_1^{\frac{1}{\lambda-1}}, \lambda \approx 4.$$

10. The X-ray dual-energy CT reconstruction method according to claim 2, wherein, in the steps (c) and (d), $r_1$ and $r_2$ are reconstructed using an ART+TV method.

11. The X-ray dual-energy CT reconstruction method according to claim 2, wherein, in the steps (c) and (d), $r_1$ and $r_2$ are reconstructed using a split Bregman method.

* * * * *